United States Patent [19]

Seitz et al.

[11] 4,418,017
[45] Nov. 29, 1983

[54] PREPARATION OF PHENYLACETONITRILES CARRYING BASIC SUBSTITUENTS

[75] Inventors: Werner Seitz, Plankstadt; Klaus Scheib, Schauernheim; Alfred Michel, Enkenbach/Alsenborn, all of Fed. Rep. of Germany

[73] Assignee: BASF Aktiengesellschaft, Fed. Rep. of Germany

[21] Appl. No.: 380,468

[22] Filed: May 20, 1982

[30] Foreign Application Priority Data

Jun. 2, 1981 [DE] Fed. Rep. of Germany ....... 3121766

[51] Int. Cl.$^3$ .......................................... C07C 121/78
[52] U.S. Cl. ............................................... 260/465 E
[58] Field of Search ................................... 260/465 E

[56] References Cited

U.S. PATENT DOCUMENTS 3,261,859  7/1966  Dengel ........................... 260/465 E

OTHER PUBLICATIONS

Tetrahedron Letters 9, (1974), pp. 707–710.

*Primary Examiner*—Dolph H. Torrence
*Attorney, Agent, or Firm*—Keil & Witherspoon

[57] ABSTRACT

Phenylacetonitriles carrying basic substituents, of the formula

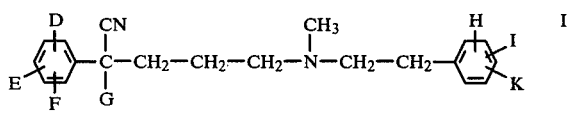

where D, E, F, G, H, I and K have the meanings given in the description, are prepared by reacting the corresponding phenylacetonitrile with a compound of the formula

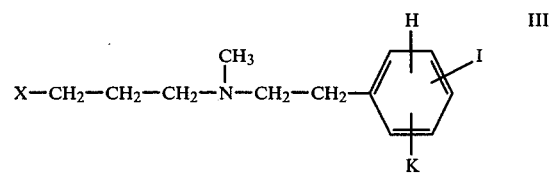

where X, H, I and K have the meanings given in the description, in a solid/liquid phase system in the presence of a phase transfer catalyst.

2 Claims, No Drawings

PREPARATION OF PHENYLACETONITRILES CARRYING BASIC SUBSTITUENTS

The present invention relates to a process for the preparation of phenylacetonitriles carrying basic substituents.

German Pat. No. 1,154,810 discloses phenylacetonitriles carrying basic substituents, of the formula

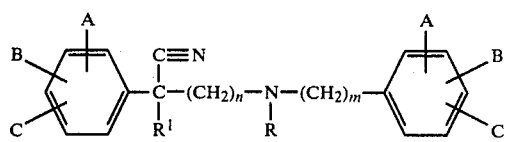

where A, B and C are hydrogen or halogen, or lower alkyl or alkoxy, and in the last-mentioned case two adjacent groups can also together form a methylenedioxy group, R is a lower aliphatic radical, $R_1$ is lower alkyl, a saturated or unsaturated cyclic or bicyclic hydrocarbon radical or benzyl or phenyl, n is 2, 3 or 4 and m is 1, 2 or 3, as substances which dilate coronary vessels.

The compounds are prepared, inter alia, by reacting a phenylacetonitrile of the formula

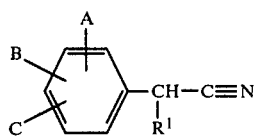

with a compound of the general formula

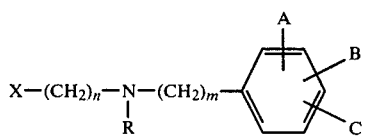

where A, B, C, R, $R^1$, n and m have the above meanings and X is a reactive acid radical, in the presence of a basic condensing agent. Sodium amide is used exclusively as the basic condensing agent for this reaction. Other basic, organometallic condensing agents, eg. butyl-lithium and lithium dialkylamides, can also be successfully used (D. S. Watt, Tetrahedron Lett. 9 (1974), 707-710). However, sodium amide and organometallic condensing agents have the disadvantage that they are very difficult to handle because they are highly sensitive towards moisture and readily flammable, which requires a high expenditure on safety, especially on an industrial scale. Moreover, the basic condensing agents required are relatively expensive, and the reactions must be carried out in absolute solvents under an inert gas. The use of sodium amide requires a reaction time of from 5 to 6 hours and a reaction temperature of 110° C., which means a higher consumption of energy and longer operating times than in the novel process. If sodium amide, sodium hydride or an organometallic reagent is used, ammonia, hydrogen and hydrocarbons respectively are formed as reaction products, which present a safety risk and/or pollute the environment.

Similar statements apply to the other processes which have been disclosed for the preparation of the above compounds (German Pat. No. 1,158,083 and German Laid-Open Applications DOS 2,059,985, DOS 2,263,527 and DOS 2,631,222).

We have now found a novel process for the preparation of the above compounds, and similar compounds, which has substantial advantages over the process described.

The present invention relates to a process for the preparation of phenylacetonitriles carrying basic substituents, of the formula I

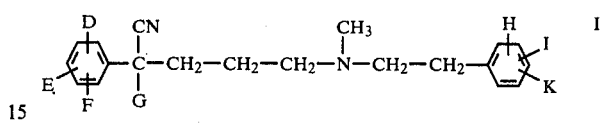

where D, E, F, H, I and K are hydrogen or halogen or alkoxy or alkyl of 1 to 4 carbon atoms and G is a straight-chain or branched aliphatic hydrocarbon radical of not more than 20 carbon atoms or a saturated or unsaturated cyclic or bicyclic hydrocarbon radical of 3 to 20 carbon atoms, by reaction of an α-substituted phenylacetonitrile of the formula II

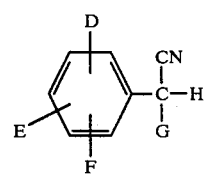

where D, E, F and G have the above meanings, with a compound of the formula III

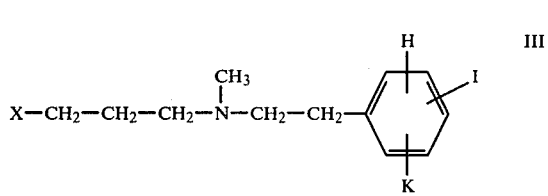

where H, I and K have the above meanings and X is chlorine, bromine or a leaving group, wherein the reaction is carried out in a solid/liquid phase system in the presence of a phase transfer catalyst.

Aromatic hydrocarbons, eg. benzene, toluene or the xylenes, have proved particularly suitable as the liquid phase for the reaction, but higher-boiling aliphatic ethers, eg. dioxane, tetrahydrofuran or dibutyl ether, can also be used.

Potassium hydroxide powder has proved to be a particularly suitable solid phase. At least three equivalents thereof are required for the reaction.

Sodium hydroxide powder is unsuitable as the solid phase for this process, since it requires long reaction times and leads to the formation of large quantities of by-product and hence to an unsatisfactory yield.

The same disadvantages are encountered in a liquid/liquid process in which a highly concentrated aqueous solution of sodium hydroxide or potassium hydroxide and a toluene solution of the two reactants are used as the liquid phases.

Suitable catalysts are symmetric quaternary tetralkylammonium or tetraalkylphosphonium salts or crown ethers. Examples are tetrabutylammonium bisulfate, bromide, iodide or chloride, 18-crown-6, dibenzo-18- crown-6 and tetrabutylphosphonium bromide or chloride. Iodides are particularly suitable.

In the form III, in addition to chlorine or bromine, X can also be a leaving group. Particularly suitable leaving groups are mesylate, tosylate and triflate ($CF_3SO_2$-).

The reaction can be carried out at from 50° to 110° C. The highest yield and the formation of the smallest amounts of by-products are achieved at from about 85° to 95° C., requiring a reaction time of about three hours.

The process according to the invention does not have the above disadvantages of the known process and gives yields of from 85 to 90% of a very pure product. These yields are far above those which have hitherto been obtained for the above compounds. Moreover, the novel process is substantially simpler than all the known processes.

EXAMPLE 1

α-Isopropyl-α-[(N-methyl-N-homoveratryl)-amino-γ-propyl]-3,4-dimethoxyacetonitrile 164 g (0.75 mole) of α-isopropylveratryl cyanide were dissolved in 100 ml of toluene at 40° C. in a three-necked flask equipped with a stirrer, dropping funnel and reflux condenser. 195 g of technical-grade potassium hydroxide powder and 1.5 g of tetrabutylammonium iodide were added to this solution. A solution of 196 g (0.75 mole) of (N-methyl-N-homoveratryl)-amino-γ-chloropropane in 150 ml of toluene was then added in the course of 45 minutes, with stirring, at a rate such that the reaction temperature did not rise above 90° C. After the addition, stirring was continued at 90° C. for 2.5 hours. 500 ml of water were added to the cooled reaction mixture, and the toluene phase was separated off and washed several times with water. The solvent was stripped off to give 350 g of crude product as a yellow oil. This oil was dissolved in 700 ml of isopropanol, and 6 M isopropanolic hydrochloric acid was added, with stirring. After 20 hours, 325 g (88%) of hydrochloride of melting point 141°–144° C. were isolated.

EXAMPLE 2

α-(n-Dodecyl)-α-[(N-methyl-N-homoveratryl)-amino-γ-propyl]-3,4-dimethoxyacetonitrile 34.5 g of α-dodecyl-veratryl cyanide were dissolved in 15 ml of toluene in the same manner as described in Example 1. 26 g of technical-grade potassium hydroxide powder, 0.2 g of tetrabutylammonium iodide and then a solution of 27 g of (N-methyl-N-homoveratryl)-amino-γ-chloropropane in 20 ml of toluene were added to this solution. Working up gave 55 g (95%) of the crude base as a yellow oil. The hydrogen oxalate of the product has a melting point of 93°–96° C. (ether).

EXAMPLE 3

α-Isopropyl-α-[(N-methyl-N-homoveratryl)-amino-γ-propyl]-3,4,5-trimethoxyphenylacetonitrile 43 g (90%) of the crude base were obtained as a yellow oil from 24.9 g (0.1 mole) of α-isopropyl-3,4,5-trimethoxyphenylacetonitrile, 27 g of (N-methyl-N-homoveratryl)-amino-γ-chloropropane, 26 g of technical-grade KOH and 0.2 g of tetrabutylammonium iodide as described in Examples 1 and 2. 44 g (85%) of the hydrochloride of melting point 145°–148° C. were isolated by dissolving the crude base in isopropanol and precipitating with HCl.

We claim:

1. A process for the preparation of phenylacetonitriles carrying basic substituents, for the formula I

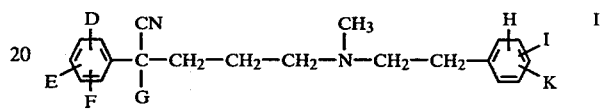

where D, E, F, H, I and K are hydrogen or halogen or alkoxy or alkyl of 1 to 4 carbon atoms and G is a straight-chain or branched aliphatic hydrocarbon radical of not more than 20 carbon atoms or a saturated or unsaturated cyclic or bicyclic hydrocarbon radical of 3 to 20 carbon atoms, by reaction of an α-substituted phenylacetonitrile of the formula II

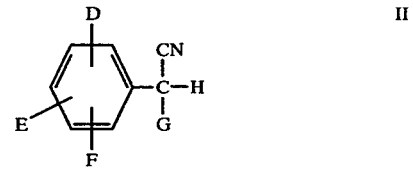

where D, E, F and G have the above meanings, with a compound of the formula III

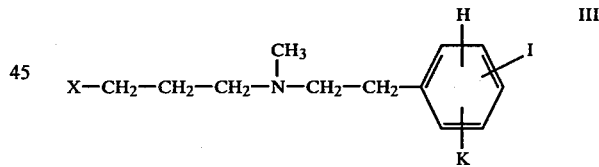

where H, I and K have the above meanings and X is chlorine, bromine or a leaving group, wherein the reaction is carried out in a solid liquid phase system in the presence of a phase transfer catalyst.

2. The process as claimed in claim 1, wherein potassium hydroxide is used as the solid phase of the solid/liquid phase system.

* * * * *

UNITED STATES PATENT AND TRADEMARK OFFICE
CERTIFICATE OF CORRECTION

PATENT NO. : 4,418,017
DATED : November 29, 1983
INVENTOR(S) : Werner SEITZ et al.

It is certified that error appears in the above-identified patent and that said Letters Patent is hereby corrected as shown below:

Claim 1, column 4, line 16, should read "in the formula I" rather than "for the formula I".

Signed and Sealed this

Third Day of April 1984

[SEAL]

Attest:

GERALD J. MOSSINGHOFF

Attesting Officer

Commissioner of Patents and Trademarks